United States Patent [19]

Barnabé

[11] 4,177,125

[45] Dec. 4, 1979

[54] ELECTROCHEMICAL DETECTOR OF THE OXYGEN CONTENT OF THE EXHAUST GASES OF COMBUSTION ENGINES

[75] Inventor: Jean-Louis M. Barnabé, Le Vesinet, France

[73] Assignee: Regie Nationale des Usines Renault, Boulogne-Billancourt, France

[21] Appl. No.: 909,494

[22] Filed: May 25, 1978

[30] Foreign Application Priority Data

May 25, 1977 [FR] France .................................. 77 15916

[51] Int. Cl.² ............................................. G01N 27/46
[52] U.S. Cl. ............................... 204/195 S; 123/119 E
[58] Field of Search .............................. 204/15, 195 S

[56] References Cited

U.S. PATENT DOCUMENTS

| | | | |
|---|---|---|---|
| 3,468,780 | 9/1969 | Fischer | 204/195 S |
| 3,481,855 | 12/1969 | Kolodnet et al. | 204/195 S |
| 3,616,407 | 10/1971 | En Gell et al. | 204/195 S |
| 3,630,874 | 12/1971 | Olette et al. | 204/195 S |
| 3,847,778 | 11/1974 | Riddel | 204/1 S |
| 3,891,529 | 6/1975 | Beesch | 204/195 S |
| 4,005,001 | 1/1977 | Pebler | 204/195 S |
| 4,021,326 | 5/1977 | Pollner et al. | 204/195 S |

FOREIGN PATENT DOCUMENTS

| | | | |
|---|---|---|---|
| 2304464 | 8/1974 | Fed. Rep. of Germany | 204/195 S |
| 2632138 | 2/1977 | Fed. Rep. of Germany | 204/195 S |

*Primary Examiner*—T. Tung
*Attorney, Agent, or Firm*—Oblon, Fisher, Spivak, McClelland & Maier

[57] ABSTRACT

An electrochemical detector for measuring the oxygen content of the exhaust gases of internal combustion engines. The detector consists of a ceramic body having a catalytic electrode and a non-catalytic electrode, both of which are exposed to the flow of the exhaust gases and are separated along the surface of the ceramic body. In one embodiment, the ceramic body is a rod. In another embodiment it takes the shape of a cone.

6 Claims, 10 Drawing Figures

ELECTROCHEMICAL DETECTOR OF THE OXYGEN CONTENT OF THE EXHAUST GASES OF COMBUSTION ENGINES

BACKGROUND OF THE INVENTION

1. Field of the Invention

The invention relates to a measuring electrochemical detector for determining the oxygen content of exhaust gases, particularly exhaust gases of internal combustion engines. It comprises an oxygen-ion conducting solid electrolyte and two metallic electrodes, one of which exhibits at the operating temperature an elevated catalytic activity, while the other electrode simply conducts electrons, is nonoxidizable, and exhibits no special catalytic activity.

2. Description of the Prior Art

The devices known up to now are generally made up of two electrodes, one of which is in contact with a gas containing oxygen at constant pressure, usually air, while the other electrode, immersed in the gases being analyzed, exhibits a marked catalytic activity at temperatures above 300° C.

SUMMARY OF THE INVENTION

It is an object of the present invention to eliminate the reference air compartment and substitute for it a reference constituted by a noncatalytic electrode in contact with the burned gases. The potential of this reference varies as a function of the richness, but its variation is less than 100 mV between the air/fuel ratios $R=0.7$ and $R=1.1$ and for temperatures between 200° C. and 600° C., which are the normal operating temperatures of catalytic devices.

The advantages of this arrangement over the preceding ones are many, and lead to considerable simplification in construction of the assembly and, consequently, a lowering of the cost of fabrication of such devices.

The electrodes may be totally immersed in the burned gases and, consequently, may be composed of tubes, plates, tori, hyperbolic paraboloids etc.

The separation into two airtight compartments in the prior art entails the use of nonporous zirconia which is very impermeable to the burned gases; according to the present invention the electrolyte may be porous and, consequently, may be obtained by fritting at a lower temperature than that for the ceramic precedents.

Preferably a ceramic is utilized that consists of zirconium oxide stabilized with 8 to 14% yttrium oxide.

The possibility of placing the reference electrode and the measuring electrode on the same surface of the ceramic eliminates the necessity of using an electrolyte through the thickness of the ceramic and thus permits reduction of the size of the latter; probes of low internal resistance can be realized by bringing the catalytic and noncatalytic surfaces close to one another.

Employing surface conductivity properties permits a reduction of the delay in operation of the probe when the motor is cold started in effect, the surface exposed to the burned gases attains a temperature above 300° C. much quicker than the entire thickness of the ceramic; the result is a significant lessening of the delay in starting up operation as well as an improvement in the temperature of the initial operation.

The electrode surface necessary to assure good performance of the present device is much smaller than that for conventional probes; it is thus possible to utilize smaller volumes of solid electrolyte, smaller electrode surfaces and, eventually, to pair-up a series of catalytic and noncatalytic electrodes to realize printed circuits delivering an output of several volts in a rich mixture, thus simplifying electronic amplification.

BRIEF DESCRIPTION OF THE DRAWINGS

Various other objects and many of the attendant advantages of the present invention will be readily appreciated as the same becomes better understood by reference to the following detailed description when considered in connection with the accompanying drawings, in which like reference characters designate the same or similar parts throughout the figures thereof and wherein.

DETAILED DESCRIPTION OF THE PREFERRED EMBODIMENTS

Figure 1:
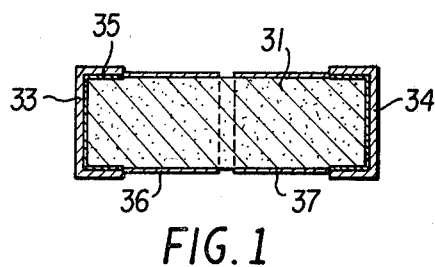
FIG. 1 is a cross section of a probe consisting of a cylindrical bar with electrodes on its ends.
Figure 2:
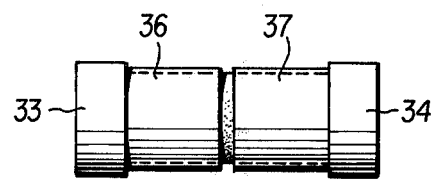
FIG. 2 is another view of the probe of FIG. 1.

FIGS. 1 and 2 show an arrangement in which the solid electrolyte consists of a cylindrical bar of zirconia stabilized with yttrium oxide.

A solid cylinder 31 of zirconia with a porosity between 5 and 25% carries on its ends two metallic caps 33-34 of inconel 600 or nickel pressed onto a conducting film 35 of silver 0.1 to $0.2\mu$ thick obtained by electrolysis and, more towards the center, two conducting electrodes 36 and 37 with a gas between them and each in contact with one of the caps, one of the electrodes being composed of silver or gold 0.1 to $0.3\mu$ thick and the other of finely divided platinum 0.5 to $2\mu$ thick. The two electrodes are advantageously covered with a porous refractory coating (not shown) consisting either of alumina or magnesium aluminate deposited by pulverization in a plasma torch, or of a sleeve of refractory and insulating fibers consisting of kaolin, silica or alumina.

Figure 3:
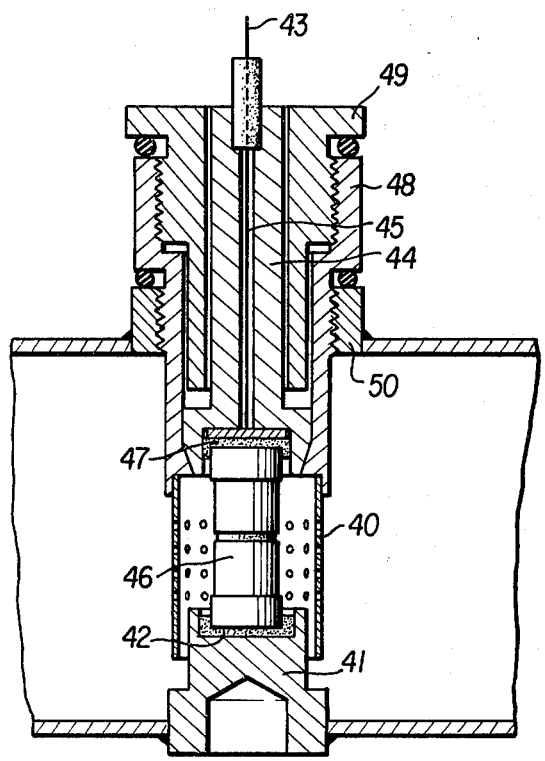
FIG. 3 is a cross section of the mounting of a probe such as that of FIG. 1 or FIG. 2.

The assembly can be mounted in the exhaust manifold with an arrangement (FIG. 3) comprising, at the end of a perforated tube 40, a support 41 fixed to the manifold, the support 41 having a recess containing a packing of inox 42 and, in addition, at the other end, an assembly for providing the electrical connection between lead 43 and the active electrode. This assembly is made up of an insulating alumina tube 44, the central part of which has an electrical conductor 45 connected to the detector 46 via an elastic conducting packing 47. The tube 50 is positioned in a body 48 and held fixed by a clamping plug 49.

The assembly is sealed by means of copper washers and screwed into a threaded receptable 50 in the manifold wall.

Figure 4:
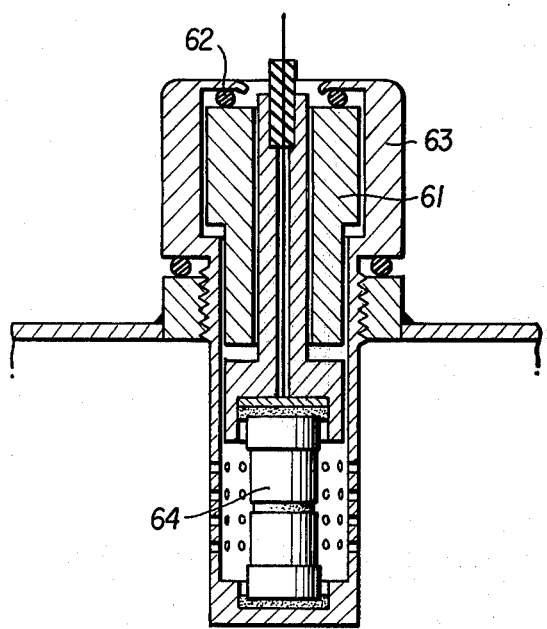
FIG. 4 is a section through a single block variant of the mounting in FIG. 3.

FIG. 4 shows a single block variant of the preceding arrangement which is in the shape of a spark plug in which the insulating body 61 is held in the body 63 by the seal 62. In this case the active element 64 is not replaceable, as it is in the mounting of FIG. 3.

Figure 5:
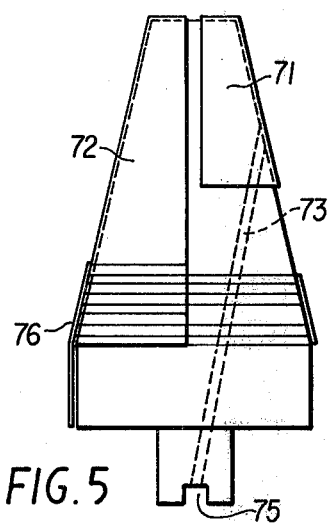
FIG. 5 is an elevation of a truncated cone-construction.
Figure 6:
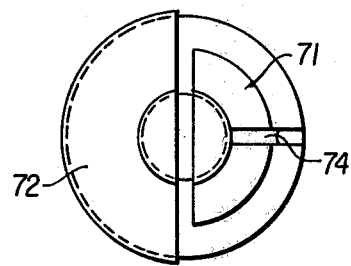
FIG. 6 is a plan view corresponding to FIG. 5.

In the form of the embodiment shown in FIGS. 5 and 6, an active ceramic is utilized consisting of zirconium oxide stabilized with 12% of yttrium oxide and having the shape of a cone or a truncated cone.

Two electrodes 71 and 72, one of which is composed of gold or silver 0.1 to 0.3 in thickness and the other of active, porous, conducting platinum 0.5 to 2 thick, are situated on the vertex face and on the lateral surface of the ceramic body and are separated by a $\sim 1$ mm gap. An internal passage 73 or a lateral groove 74 permits transmissions of the voltage from the active electrode to the contact 75, while a ring of conducting metal 76, 0.1 mm thick and nonporous, provides the electrical connection between the neutral electrode and the system ground. This ring may consist of silver or an alloy of copper and lead (rose metal).

Figure 7:
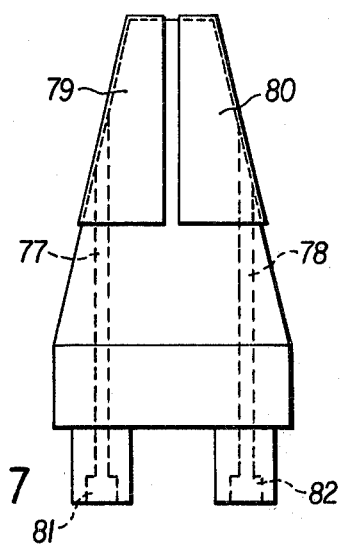
FIG. 7 is a view in elevation of a variant of the configuration in FIG. 5.
Figure 8:
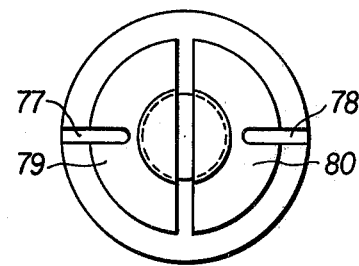
FIG. 8 is a plan view corresponding to FIG. 7.

FIGS. 7 and 8 present a variant of FIG. 5 which avoids grounding the reference electrode. It utilizes two notches 77, 78 inside each of which is deposited a filament of conducting silver or platinum, permitting transmission of the corresponding voltages of the electrodes 79, 80 to the contacts 81, 82. These notches may possibly be replaced by narrow passages of 0.5 to 2 mm diameter, and the electrodes are separated by a minimum gap of 0.5 mm which may be constant or alternatively which may go through a minimum at the summit of the truncated cone.

Figure 9:
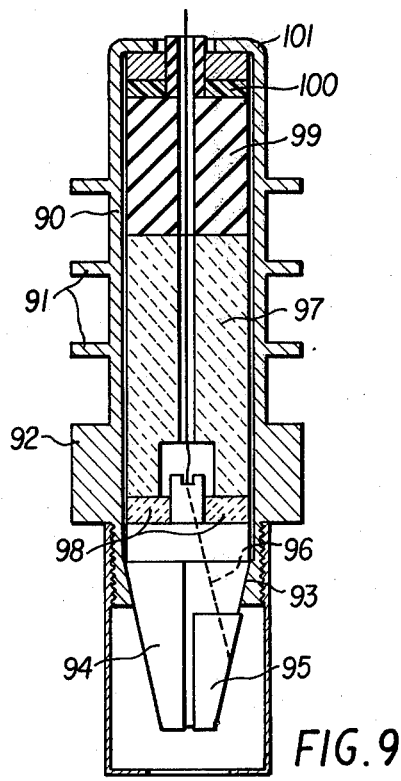
FIG. 9 is a section through a mounting of the probe of FIG. 5 of FIG. 7.
Figure 10:
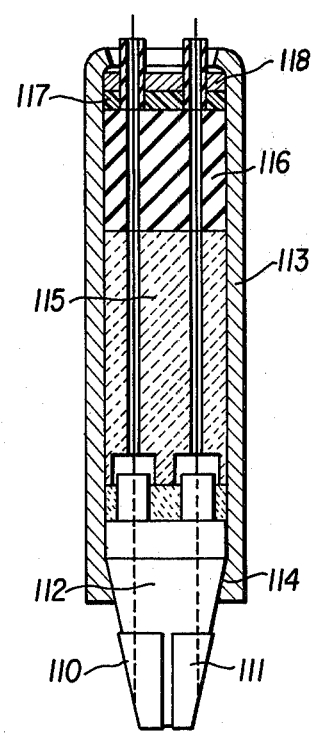
FIG. 10 is a section through a variant of the mounting in FIG. 9.

The active elements of FIGS. 5 and 7 may each be mounted in an envelope shown in FIGS. 9 and 10 which may be closed off and which is comprised of a body 90 which may or may not be furnished with cooling fins 91. This body is screwed onto the exhaust with the help of the head 92. It comprises a conical part 93 which provides the electrical contact of the neutral electrode 94, while the active electrode 95 is connected to a platinum wire conductor 96. An electrical insulator 97 is traversed by this wire and presses against a packing 98 made up of insulating ceramic or possibly conducting metallic fibers intended to provide a quasi-isostatic pressure on the lower face of the active element and to hold it in position.

An elastic insulating element 99 of silicone rubber takes care of the compression of the assembly and compensates for thermal expansion as well as damping mechanical vibrations. Its temperature of decomposition which is below 300° C., entails the use of cooling fins or the use of a probe body between 50 and 100 mm long. An insulating washer 100 of rigid bakelite and a metal washer 101 hold the assembly under compression.

FIG. 10 presents a variant of this arrangement in which the cooling fins and mounting threads have been eliminated and which exhibits two electrical contacts independent of a ground.

The probe of FIG. 7 has electrodes 110, 111 mounted on the porous zirconia electrolyte 112. It sits in the body 113 on a conical part 114 against which it is pressed by a cylindrical insulating and refractory element 115 intended to provide passage and electrical insulation for the electrical leads. Element 115 maintains pressure on the probe and thermally insulates the elastic element 116, which consists of an insulating silicone rubber plug through which pass two electrical leads and which is intended to provide compression, to compensate for thermal expansion, and to dampen mechanical vibrations of the unit.

A rigid bakelite insulator 117 and, a rigid metallic washer 118 perforated by two holes, permit the tightening or damping of the body 113 under pressure.

The porous ceramic body may also have the shape of another body of revolution such as a sphere, a torus, or a hyperbolic paraboloid.

Obviously, many modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An electronic detector for detecting the oxygen content of the burned gases of a combustion engine, said detector comprising:
   two electrode bodies on the surface of a porous ceramic body, said porous ceramic body being composed of zirconium oxide stabilized with between 8% and 14% yttrium oxide;
   one of said electrodes being composed of a metal exhibiting no catalytic activity;
   the other of said electrodes being composed of porous platinum of a thickness between 0.5 and $2\mu$;
   said ceramic body being defined by a body of revolution which is positioned in a metallic housing; said metallic housing being attached to an exhaust manifold and having at least one passage for at least one lead connected to at least one of said electrodes, said ceramic body being held in said metallic housing in a semi-rigid condition by an elastic packing;
   a silicone rubber plug located in the coolest part of said housing body for damping vibrations and compensating for thermal expansion; and
   cooling fins on said housing for avoiding overheating of said plug;
   wherein said electrodes are located in the flow of burned gases and the richness of carburization is measured by determining the difference in potential between the electrode exhibiting a significant catalytic activity and that exhibiting none.

2. A detector as in claim 1, characterized by the fact that the ceramic body conducts oxygen and exhibits a porosity between 5 and 25% at its surface.

3. A detector as in claim 1, characterized by the fact that the ceramic body conducts oxygen ions and is in the shape of a cylindrical rodlike assembly each end of which is enclosed by a metal cap, said assembly being mounted under compression in said metallic housing.

4. A detector as in claim 1, characterized by the fact that the ceramic body conducts oxygen ions and has the shape of a cone or a truncated cone.

5. A detector as in claim 1, characterized by the fact that the ceramic body conducts oxygen ions and is in the form of a sphere of a hyperbolic paraboloid.

6. A detector as in claim 1, in which the ceramic body has a plurality of catalytic electrodes disposed in series and a plurality of non-catalytic electrodes disposed in a second series.

* * * * *